United States Patent [19]

Chorvat

[11] 4,230,626

[45] Oct. 28, 1980

[54] 25-HALOCHOLEST-5-ENE-3β,22-DIOLS AND ESTERS THEREOF

[75] Inventor: Robert J. Chorvat, Arlington Heights, Ill.

[73] Assignee: G. D. Searle & Co., Skokie, Ill.

[21] Appl. No.: 61,731

[22] Filed: Jul. 30, 1979

[51] Int. Cl.² ............................................... C07J 9/00
[52] U.S. Cl. ................................................. 260/397.2
[58] Field of Search ..................................... 260/397.2; /Steroids MS File

[56] References Cited

U.S. PATENT DOCUMENTS 4,069,321   1/1978   Jones et al. ................. 260/239.55 R

OTHER PUBLICATIONS

J. Biol. Chem. 248 (1973), p. 8408.

*Primary Examiner*—Elbert L. Roberts
*Attorney, Agent, or Firm*—James R. Henes

[57] ABSTRACT

25-Halocholest-5-ene-3β,22-diols and esters thereof which inhibit the activity of 3-hydroxy-3-methylglutaryl coenzyme A reductase and inhibit the formation of serum cholesterol and their preparation from 3α,5-cyclo-6β-methoxy-23,24-dinor-5α-cholan-20-al are disclosed.

5 Claims, No Drawings

25-HALOCHOLEST-5-ENE-3β,22-DIOLS AND ESTERS THEREOF

This invention relates to 25-halocholest-5-ene-3β,22-diols and esters thereof. More particularly, this invention relates to new, useful, and unobvious chemical compounds of the formula

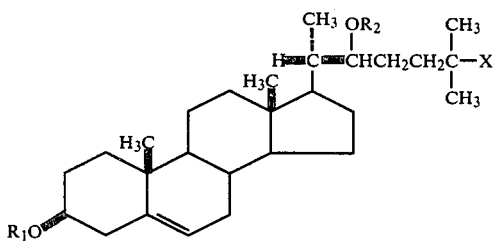

wherein X represents a halogen having an atomic number less than 53, preferably fluorine; $R_1$ and $R_2$ may be the same of different and each represents hydrogen or an esterifying moiety of the formula

wherein n represents an integer from 1 to 3, namely, 2-carboxyl-1-oxoethyl, 3-carboxyl-1-oxopropyl, and 4-carboxyl-1-oxobutyl.

The compounds to which this invention relates are useful by reason of their valueable pharmacological properties. Thus, for example, they inhibit the activity of 3-hydroxy-3-methylglutaryl coenzyme A (HMG CoA) reductase, an enzyme which controls the rate at which cholesterol is synthesized in mammalian liver (one of the two principal sources of serum cholesterol). Thus, the compounds of this invention inhibit the formation of serum cholesterol. The innovative significance of compounds adapted to inhibit sterol biosynthesis in individuals predisposed to familial type II hypercholesterolemia (WHO classification) is widely recognized. See, for example, Breslows et al., Biochem. et Biophys. Acta, 398, 10 (1975); Betteridge et al., Brit. Med. J., 4, 500 (1975); and Brown et al., J. Biol Chem., 249, 7306 1 (1974).

The HMG CoA reductase-inhibitor activity of the instant compounds and their inhibition of the formation of serum cholesterol can be demonstrated via the following standardized test procedure; Male Charles River CD rats initially weighing 180–250 g apiece, are randomized in groups of 6, housed in a reverse light cycle (12:12) room, and maintained therein on a standard rat diet plus water ad libitum. To each animal in a group, after at least 3 but not more than 6 days, 5 mg/kg of 20,25-diazacholesterol dissolved in 0.2 ml of physiological saline containing 0.1% of polyoxyethylene sorbitan monooleate (Tween 80) is intragastrically administered on each of 7 consecutive days, during the last 4 of which test compound is concurrently and identically administered at a pre-selected daily dose (commonly 5 mg/kg intragastrically). Controls are provided by a second group of animals identically treated except that test compound is omitted. Within 2–4 hr after treatment is completed, and 5–7 hr into the dark cycle, the animals are anesthetized with 1,1'-oxybisethane and thereupon killed. Livers are quickly removed, washed with a chilled homogenization medium (preparable by dissolving 102.7 g of sucrose, 3.8 g of sodium edetate, and 0.8 g of dithiothreitol in water q.s. 1000 ml), blotted dry, weighed, and homogenized (using 2 ml of the aforesaid chilled medium for each g of liver). The homogenates are centrifuged at 4° C. and 15,000×g for 15 min., whereupon the supernatants are separated and centrifuged 4° C. and 100,000×g for 60 min. The resultant supernatants are discarded and the residues suspended in half the volume of homogenization medium previously employed (i.e., 1 ml for each g of residue). HMG CoA reductase activity is assayed substantially in accordance with procedures described by L. W. White et al. in Biochemistry, 9, 2713 (1970); M. S. Brown et al. in J. Biol. Chem., 248, 4731 (1973); and P. A. Edwards et al. in Biochim. Biophys. Acta, 409, 39 (1975). Protein is determined by the method of O. H. Lowry et al., J. Biol. Chem., 193, 265 (1951). The data obtained are converted to specific activity (nmol/20 min./mg protein) for each animal, from which group mean(s) and percent change, relative to controls, are calculated. A statistically significant response ($P \leq 0.05$) is the criterion for HMG CoA reductase inhibition/stimulation.

One of the preferred embodiments of this invention, 25-fluorocholest-5-ene-3β,22-diol, was found to inhibit HMG CoA reductase activity in the foregoing test by 45, 45, 34, 50 and 3% at 25, 10, 5, 1 and 0.5 mg/kg, respectively, when administered intragastrically as hereinbefore described. The inhibitory activity in the 05–25 mg/kg dosage range is the more remarkable because cholest-5-ene-3β,22-diol stimulated HMG CoA reductase by 24% at 30 mg/kg when administered intragastrically under the same conditions.

The distinguishing response to 25-fluorocholest-5-ene-3β,22-diol in rats set forth above is of course intended merely to illustrate this aspect of the instant invention, and accordingly is not to be construed as either delimiting or exclusionary.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl ethers, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved or suspended in water or a comparably innocuous liquid. Parenteral administration may be effected via sterile fluid admixture with water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art: see, for example, F. W. Martin et al., "Remington's Pharmaceutical Sciences", 14 Ed., Merck Publishing Company, Eaton, Pa., 1965.

Appropriate dosages, in any given instance, of course, depend upon the nature and severity of the condition treated, the route of administration, and the species of mammal involved, including its size and any individual idiosyncrasies which obtain.

Preparation of compounds of this invention proceeds variously as follows: 3α,5-cyclo-6β-methoxy-23,24-dinor-5α-cholan-20-al [described in Hutchins, Thompson and Svoboda, Steroids, 15, 113 (1970)] of formula I

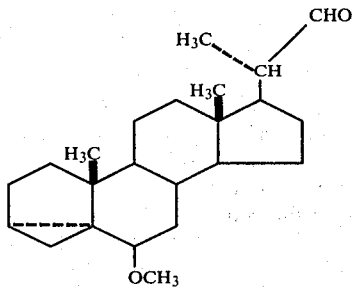

is contacted in cold tetrahydrofuran under nitrogen with a Grignard reagent of the formula

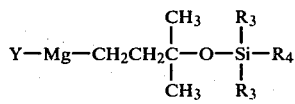

in which Y represents chlorine or bromine, preferably chlorine, and $R_3$ and $R_4$ may be the same or different and each represents a straight-chain or branched-chain alkyl containing 1 to 4 carbon atoms, whereupon aqueous ammonium chloride is added to the mixture.

The Grignard reagent is prepared by treating ethyl 3-halopropionate, preferably 3-chloropropionate, with excess methylmagnesium halide to afford the tertiary carbinol of formula III. This

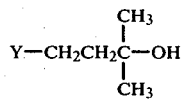

alcohol was then protected as the silyl ether by treatment with a tri-lower-alkyl-substituted silyl halide, for example, trimethylsilyl chloride, in dimethylformamide in the presence of imidazole, to afford the corresponding silyl ether of formula IV. Reaction of the protected

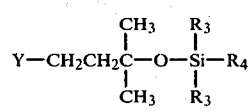

carbinol with magnesium turnings in dry tetrahydrofuran provides the desired Grignard reagent of formula II.

From the reaction of the Grignard reagent and 3α,5-cyclo-6β-methoxy-23,24-dinor-5α-chlolan-20-al, the resultant i-steroid alcohol, of formula V

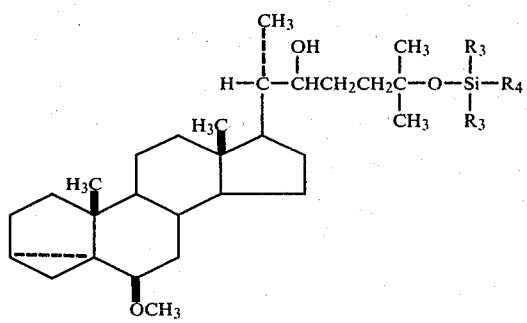

is rearranged and hydrolyzed by heating in aqueous dioxane with an acid such as 4-methylbenzenesulfonic acid monohydrate, giving rise to a triol of formula VI.

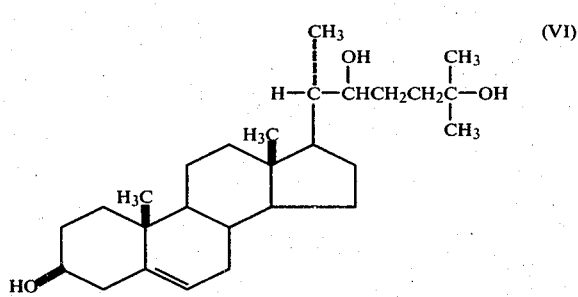

Treating a compound of formula VI in pyridine with an alkanoic acid anhydride or chloride, for example, of acetic, propanoic or butanoic acid, affords a mixture of esters of the invention having formulas VII and VIII.

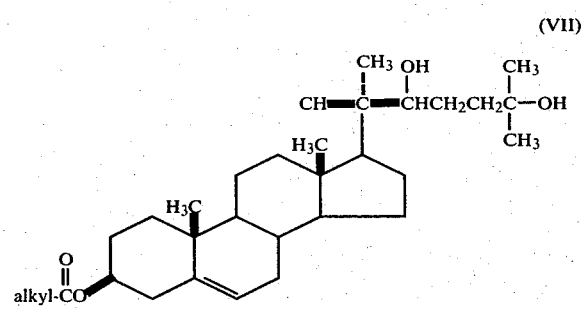

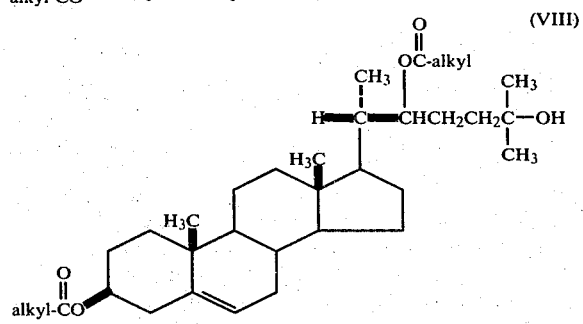

separable via chromatography on silica gel, using methylbenzene and mixtures thereof with increasing amounts of ethyl acetate as eluting solvents Treating a diester of formula VIII, preferably the diacetoxy ester, with a halogenating agent affords the corresponding halide of formula IX. In formula IX, X represents a fluoro, chloro or bromo radical.

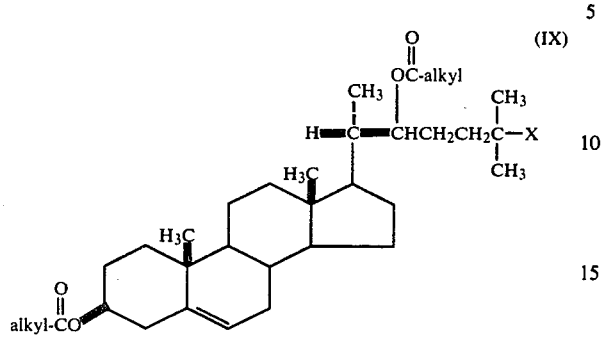

For example, treatment of a diester of formula VIII with diethylamino-sulfur trifluoride affords a compound of formula IX where X is a fluoro radical. Similarly treatment of the aforementioned diester of formula VIII with a thionyl halide and zinc halide affords the corresponding halide of formula IX. Thus, compounds of formula IX wherein X is a chloro or bromo radical could be formed by treatment of the diester of formula VIII with thionyl chloride and zinc chloride or with thionyl bromide and zinc bromide, respectively. Basic hydrolysis of the diesters of formula IX produces diols of formula X

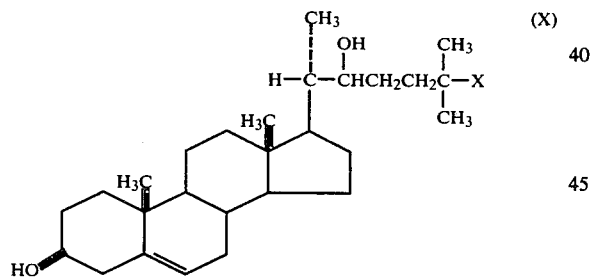

Heating a compound of formula X in pyridine with a methyl Ω-chloro-Ω-oxoalkanoate, for example, methyl-3-chloro-3-oxomalonate, methyl-4-chloro-4-oxosuccinate or methyl-5-chloro-5-oxoglutarate, affords a mixture of mixed esters having formula XI and XII

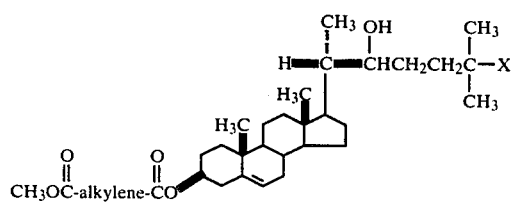

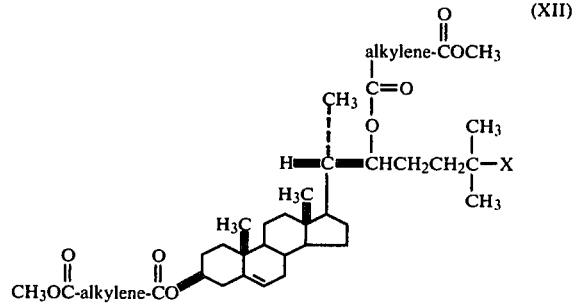

which are separable by chromatography on silica gel as aforesaid, and heating an ester of formula XI or XII with lithium iodide in pyridine, 2,6-dimethylpyridine, or 2,4,6-trimethylpyridine, or treatment with trimethylsilyl iodide and subsequent hydrolysis of the resulting silylester affords an ester of the invention having formulas XIII and XIV, respectively.

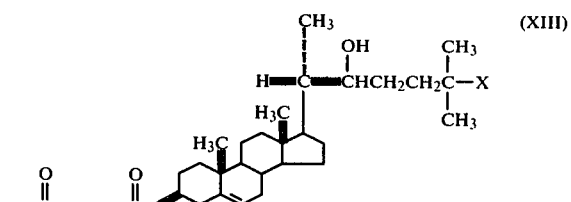

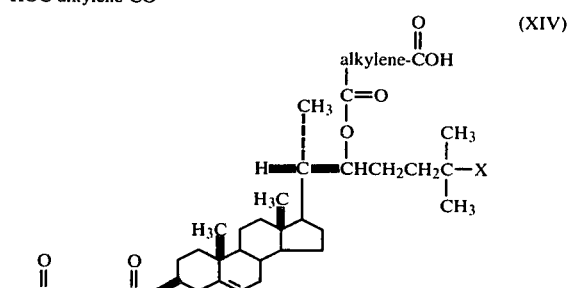

respectively. Heating a compound of formula XI or XIV with sodium bicarbonate in aqueous ethanol affords a 22-ester of the invention having formula XV

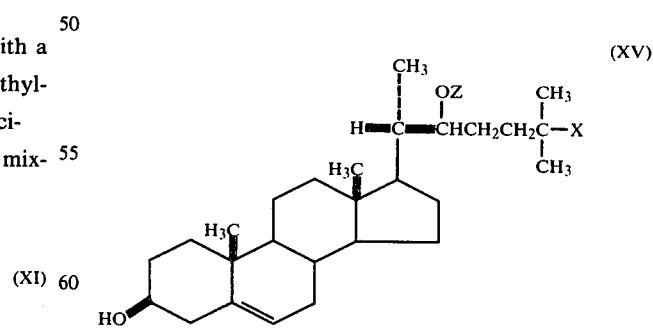

wherein Z represents 1-oxoalkyl or Ω-carboxyl-1-oxoalkyl, respectively. Finally, heating a compound of formula XI in pyridine with an alkanoic acid anhydride or chloride affords a mixed ester of the invention having formula XVI,

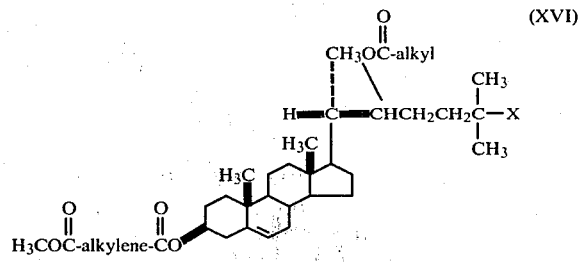

(XVI)

the methylester of which can be hydrolyzed as described above.

As an exception to the foregoing procedure, a compound of formula XIII wherein the esterifying moiety is 3-carboxy-1-oxopropyl is preferably prepared by heating a compound of formula VI with succinic acid anhydride in pyridine. In each of formulas VII, VIII, XV and XVI hereinbefore, alkyl represents methyl, ethyl or propyl. In each of formulas XI through XIV and XVI hereinbefore, alkylene representss methylene, ethylene or trimethylene.

The following examples describe in detail compounds illustrative of the present invention and methods which have been devised for their preparation, It will be apparent to those skilled in the art that many modifications, both of materials and of methods, may be practiced without departing from the purpose and intent of this disclosure. Throughout the examples hereinafter set forth, relative amounts of materials are given in parts by weight, except as otherwise noted.

EXAMPLE 1

To a solution of 27.3 parts of ethyl 3-chloro-propionate in 135 parts of tetrahydrofuran at about −20° C. under a nitrogen atmosphere was slowly added 50 parts of methyl magnesium bromide in an ether solution. After the reaction mixture was allowed to warm to room temperature, it was stirred for 4 hours. A saturated aqueous solution of ammonium chloride and ether were added to the reaction mixture, followed by the addition of sufficient 1 N hydrochloric acid solution to dissolve and inorganic salts present and allow separation of aqueous and organic phases. The aqueous phase was extracted with ether, and the ether extract was washed with a saturated aqueous solution of sodium chloride and dried over sodium sulfate. Removal of the solvent yielded an oil which after distillation under reduced pressure afforded 3-chloro-1,1-dimethylpropanol which had a boiling point of about 75°–85° C. at 1.4–1.5 millimeters of mercury pressure.

EXAMPLE 2

To a solution of 7.3 parts of the product of Example 1 in about 35 parts of dimethylformamide containing 7.35 parts of trimethylsilyl chloride was added 4.1 parts of imidazole, with heat being evolved. Thereafter the reaction mixture was stirred at room temperature for an additional 2.5 hours and then was combined into ice water. After extraction with pentane, the aqueous phase was separated and was extracted again with pentane and the combined pentane extracts were washed with a saturated aqueous solution of sodium chloride and then dried over sodium sulfate. Removal of the solvent yielded an oil which had the following formula and, after being stored over 4 Å moleculear sieve for 6 days, was dry and was used without further purification.

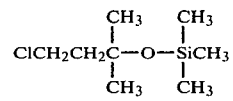

EXAMPLE 3

A solution of 3.88 parts of the product of Example 2 in 9 parts of tetrahydrofuran was combined with 0.5 parts of magnesium turnings as well as crystalline iodine, ethylene dibromide and about 0.1 part of methyl magnesium bromide. This reaction mixture was refluxed for about 1 hour, thereby forming the Grignard reagent of formula II wherein Y is chlorine and $R_3$ and $R_4$ are both methyl groups. After being cooled to room temperature, the product was diluted with 4.5 parts of tetrahydrofuran to aid the solubility of the Grignard reagent. This solution was then used as the Grignard reagent in subsequent reactions.

EXAMPLE 4

To a solution of 1.2 parts of freshly prepared 3α,5-cyclo-6β-methoxy-23,24-dinor-5α-cholan-20-al (prepared in accordance with the procedure of Hutchins, Thompson and Svoboda, Steroids, 15, 113 (1970)) in 13.5 parts of tetrahydrofuran at room temperature and under a nitrogen atmosphere was added slowly a sufficient amount of the Grignard reagent formed in Example 3 to give a positive response in the Gilman Test indicating active Grignard reagent. After stirring the reaction mixture at room temperature for 90 minutes, a saturated aqueous solution of ammonium chloride was added to hydrolyze the reaction mixture. Then sufficient ethyl ether was added to permit formation and separation of aqueous and ether phases. The separated aqueous phase was extracted with ethyl ether a second time, and the combined extracts were washed with a saturated aqueous solution of sodium chloride and then dried over sodium sulfate. Removal of the ether solvent left an oil containing a product of the following formula which was used for subsequent reaction without further purification

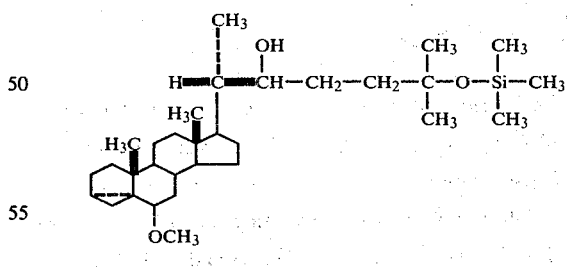

EXAMPLE 5

A solution of 2.2 parts of the product of Example 4.2 parts of hydrated tosyl acid and 20 parts of dioxane in 5 parts of water was heated on a steam bath for 1.5 hours and then cooled to room temperature, at which point an aqueous solution containing 5% by weight of sodium bicarbonate and an aqueous solution of sodium chloride were added to the reaction mixture. The reaction mixture was then extracted with chloroform and the extract was washed with an aqueous solution of sodium chloride and then dried over sodium sulfate. Removal of the solvent under reduced pressure yielded a triol product of the following formula which, after recrystallization from methanol containing a small amount of water, melted at about 181°–184° C.

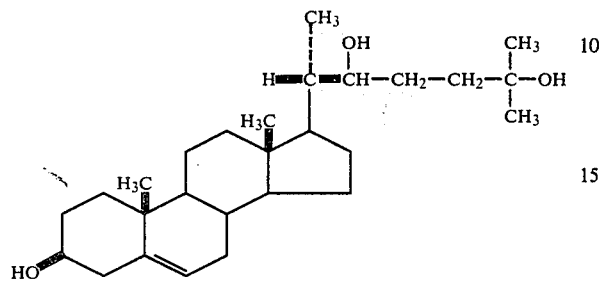

EXAMPLE 6

A solution of 3.7 parts of the triol produced in Example 5, 22 parts of acetic anhydride and 40 parts of pyridine was allowed to sit at room temperature for 18 hours. Water was then added and the precipitate which formed was collected and recrystallized from methanol. This recrystallized product was dried at 112° C. under high vacuum for 2 hours. The dried diacetoxy alcohol product had a melting point of about 169°–171° C. and was of the formula

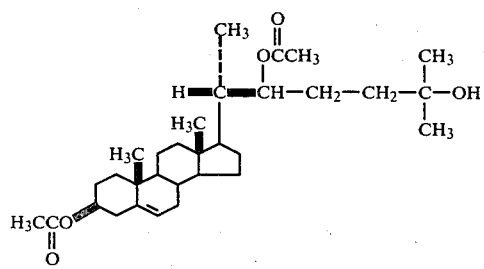

EXAMPLE 7

To a solution of 2.9 parts of the diacetoxy alcohol product of Example 6 in 64 parts of methylene chloride at −70° C. and under a nitrogen atmosphere was added dropwise 1.5 parts of diethylamino sulfur trifluoride in 12.7 parts of methylene chloride. After stirring this reaction mixture at −70° C. for 20 minutes, the solution temperature was allowed to rise and water was added to hydrolyze any excess diethylamino sulfur trifluoride and to permit aqueous and organic phases to form and be separated. The separated aqueous phases was extracted with methylene chloride and the extract was washed with an aqueous solution of 5% by weight of sodium bicarbonate and with an aqueous solution of sodium chloride and then was dried over sodium sulfate. Removal of the methylene chloride solvent left a diacetate fluoride of formula

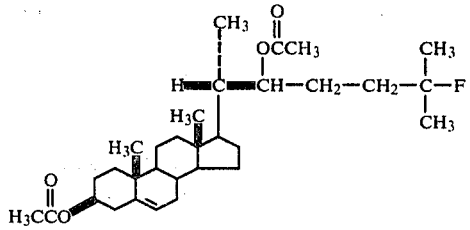

which, after recrystallization from methanol containing a small amount of water, melted at about 161°–162° C.

EXAMPLE 8

A solution of 2.5 parts of the product of Example 7, 1 part of sodium hydroxide, 19 parts of water and 64 parts of methanol was refluxed for 4 hours. Upon cooling this reaction mixture to room temperature, a product of formula

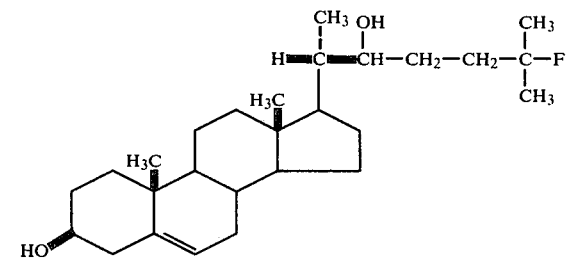

crystallized and was collected. Upon recrystallation from methanol containing a small amount of water the product had a melting point of about 162°–163° C. after drying at 80° C. under a high vacuum for 3.5 hours.

EXAMPLE 9

A solution of 4 parts of the product of Example 8 in 60 parts of pyridine was combined with 3 parts of succinic anhydride, and this reaction mixture was heated on a steam bath for about 16 hours. After being cooled to room temperature, the reaction mixture was added to 1000 parts of water which was then extracted with ethyl acetate. The ethyl acetate extract was washed with water, 5% by weight of hydrochloric acid in water, and a saturated aqueous solution of sodium chloride and then dried over anhydrous magnesium sulfate. After filtering the dried extract, the ethyl acetate solvent was removed under reduced pressure, leaving a product of formula

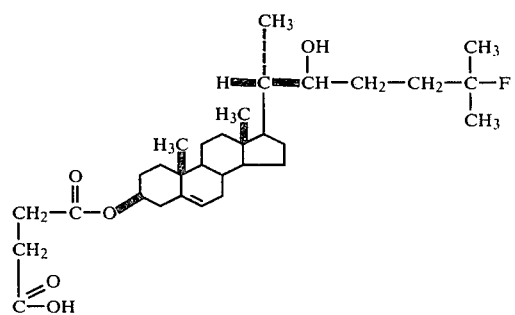

which, after recrystallization from methanol containing a small amount of water, had a melting point of about 150°–154° C.

EXAMPLE 10

To a solution of 8.5 parts of the product of Example 6 and 3.3 parts of zinc chloride in 450 parts of benzene was added 10 parts of thionyl chloride and this reaction mixture was stirred at room temperature for 2 hours. Then a sufficient volume of 5% by weight of sodium bicarbonate in water was added to the reaction mixture to permit the formation and separation of aqueous and organic phases. The separated benzene phase was washed with water and with a saturated aqueous solution of sodium chloride and then dried over sodium sulfate. Removal of the solvent from the dried benzene phase left a product having the following formula which, after recrystallization from methanol containing a small amount of water and drying at 110° C. under reduced pressure for 2.5 hours, had a melting point of about 174°–176° C.

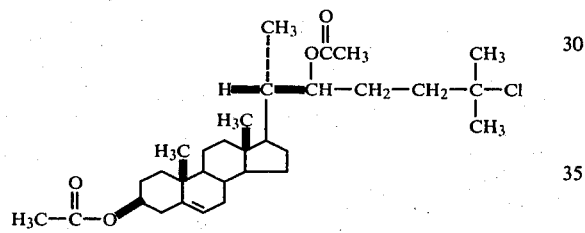

EXAMPLE 11

The procedure of Example 8 is repeated using the product of Example 10 instead of the product of Example 7 to afford a product of formula

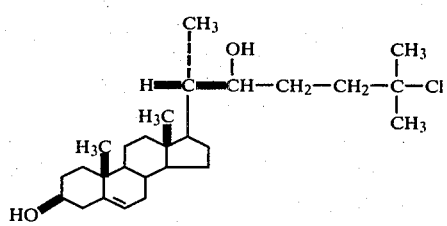

EXAMPLE 12

The procedure of Example 9 is repeated using the product of Example 11 instead of the product of Example 8, to afford a product of formula

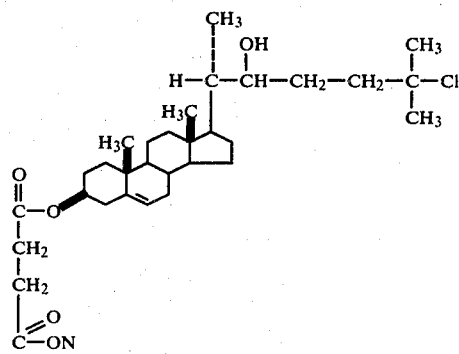

What is claimed is:
1. A compound of the formula

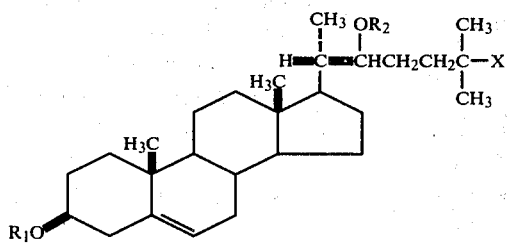

wherein X represents a halogen having an atomic number less than 53 and $R_1$ and $R_2$ may be the same or different and each represents hydrogen or a radical of the formula

in which n represents an integer from 1 to 3.

2. A compound according to claim 1 wherein X is fluorine.

3. A compound according to claim 1 which is 25-fluorocholest-5-ene-3β,22-diol.

4. A compound according to claim 1 which is 25-fluorocholest-5-ene-3β,22-diol 3-(hydrogen butanedioate).

5. A compound according to claim 1 which is 25-fluorocholest-5-ene-3β,22-diol 3-(hydrogen propanedioate).

* * * * *